(12) United States Patent
Glossop et al.

(10) Patent No.: US 8,632,468 B2
(45) Date of Patent: Jan. 21, 2014

(54) METHOD, SYSTEM AND DEVICES FOR TRANSJUGULAR INTRAHEPATIC PORTOSYSTEMIC SHUNT (TIPS) PROCEDURES

(75) Inventors: Neil David Glossop, Toronto (CA); Bradford Johns Wood, Potomac, MD (US); Thomas S. Y. Tang, Markham (CA)

(73) Assignee: Koninklijke Philips N.V., Eindhoven (NL)

( * ) Notice: Subject to any disclaimer, the term of this patent is extended or adjusted under 35 U.S.C. 154(b) by 773 days.

(21) Appl. No.: 12/392,817

(22) Filed: Feb. 25, 2009

(65) Prior Publication Data

US 2010/0217117 A1   Aug. 26, 2010

(51) Int. Cl.
  *A61B 8/14*   (2006.01)
(52) U.S. Cl.
  USPC ........... 600/464; 600/424; 600/437; 600/459; 600/462
(58) Field of Classification Search
  None
  See application file for complete search history.

(56) References Cited

U.S. PATENT DOCUMENTS

| | | | |
|---|---|---|---|
| 5,211,165 A * | 5/1993 | Dumoulin et al. | 600/410 |
| 5,638,819 A * | 6/1997 | Manwaring et al. | 600/424 |
| 5,830,222 A * | 11/1998 | Makower | 606/159 |
| 5,840,025 A * | 11/1998 | Ben-Haim | 600/424 |
| 6,064,904 A * | 5/2000 | Yanof et al. | 600/414 |
| 6,148,095 A * | 11/2000 | Prause et al. | 382/131 |
| 6,332,089 B1 | 12/2001 | Acker et al. | |
| 6,470,207 B1 * | 10/2002 | Simon et al. | 600/426 |
| 6,535,756 B1 * | 3/2003 | Simon et al. | 600/424 |
| 6,591,129 B1 | 7/2003 | Ben-Haim et al. | |
| 6,616,610 B2 * | 9/2003 | Steininger et al. | 600/443 |
| 6,655,386 B1 * | 12/2003 | Makower et al. | 128/898 |
| 6,660,024 B1 * | 12/2003 | Flaherty et al. | 600/439 |
| 6,671,538 B1 * | 12/2003 | Ehnholm et al. | 600/425 |
| 6,782,288 B2 * | 8/2004 | Truwit et al. | 600/429 |
| 6,785,571 B2 * | 8/2004 | Glossop | 600/424 |
| 7,176,936 B2 * | 2/2007 | Sauer et al. | 345/592 |
| 7,319,897 B2 * | 1/2008 | Leitner et al. | 600/424 |
| 7,660,623 B2 * | 2/2010 | Hunter et al. | 600/424 |
| 7,662,128 B2 * | 2/2010 | Salcudean et al. | 604/93.01 |
| 7,809,176 B2 * | 10/2010 | Gundel | 382/128 |
| 7,811,294 B2 * | 10/2010 | Strommer et al. | 606/108 |
| 7,822,458 B2 * | 10/2010 | Webster et al. | 600/407 |
| 7,966,057 B2 * | 6/2011 | Macaulay et al. | 600/424 |
| 7,967,742 B2 * | 6/2011 | Hoeg et al. | 600/103 |

(Continued)

FOREIGN PATENT DOCUMENTS

WO    WO9729682    8/1997
WO    WO02062265   8/2002

*Primary Examiner* — Long V. Le
*Assistant Examiner* — Bradley Impink

(57) ABSTRACT

Systems and methods for assisting/performing image-guided transjugular intrahepatic portosystemic shunt (TIPS) procedures in a portion of an anatomy of a patient include a guide needle portion having a hollow tube with a bend toward its distal tip, and a puncture needle portion that includes at least one position indicating element at its tip. The puncture needle is slidably mounted within the hollow tube of the guide needle such that a distal tip of the puncture needle can be extended from an opening in the distal tip of the guide needle and used to place a shunt between the portal and hepatic veins of a patient. The position indicating element of the puncture needle is used to produce a display of the puncture needle relative to a target vessel, including a projected path of the puncture needle that can be adjusted to accurately locate a shunt.

18 Claims, 13 Drawing Sheets

(56) References Cited

U.S. PATENT DOCUMENTS

| | | |
|---|---|---|
| 2003/0220557 A1 | 11/2003 | Cleary et al. |
| 2004/0267121 A1* | 12/2004 | Sarvazyan et al. ............ 600/439 |
| 2006/0167416 A1* | 7/2006 | Mathis et al. ............ 604/164.01 |
| 2006/0184011 A1* | 8/2006 | Macaulay et al. ............ 600/423 |
| 2008/0171934 A1 | 7/2008 | Greenan et al. |
| 2009/0118640 A1* | 5/2009 | Miller et al. .................. 600/567 |
| 2011/0270270 A1* | 11/2011 | Vancamberg et al. ........ 606/130 |

\* cited by examiner

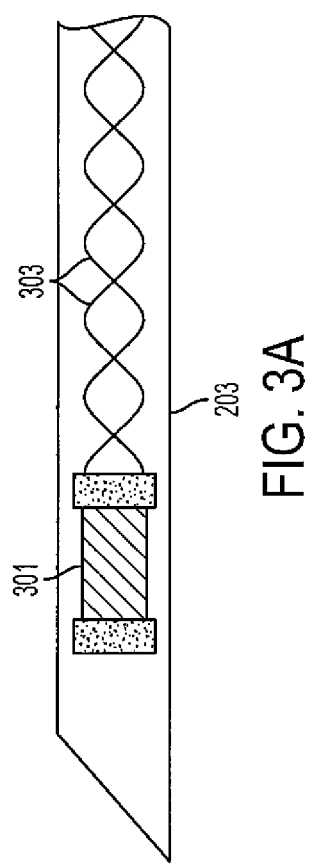

METHOD, SYSTEM AND DEVICES FOR TRANSJUGULAR INTRAHEPATIC PORTOSYSTEMIC SHUNT (TIPS) PROCEDURES

STATEMENT OF GOVERNMENT RIGHTS

The Government of the United States of America may have certain rights in the invention disclosed and claimed below.

FIELD OF THE INVENTION

This invention relates to methods, systems and devices for assisting or performing an image-guided transjugular intrahepatic portosystemic shunt (TIPS).

BACKGROUND OF THE INVENTION

Transjugular intrahepatic portosystemic shunt (TIPS) procedures are typically performed to attempt to connect the portal and hepatic veins in the liver in an effort to reduce portal hypertension (i.e. high blood pressure of the portal system of the liver). Typical systems and methods for performing TIPS procedures have shortcomings that do not solve the central problems associated with the procedure. The procedure is currently performed by using fluoroscopic images to introduce a long needle called a "Colapinto" needle into the hepatic vein. Once in place, a blind needle stick is made through the hepatic vein wall, through the liver parenchyma toward the portal vein in an attempt to connect the two vessels.

Conventional TIPS systems use a puncture needle that is encased in a large hollow guide needle bent at an angle that is appropriate for most TIPS procedures. The correct shunt path is determined by blindly passing the puncture needle in the perceived direction of the target vessel and slowly retracting it while applying negative pressure to a syringe attached to the puncture needle or its hollow cannula and checking to see if blood is returned, indicating a vessel has been struck. The procedure continues by placing a guide-wire through the puncture needle and confirming its path using fluoroscopy. Once confirmed, a series of dilators and/or a balloon is inflated over the guide-wire and a stent is inserted and expanded to establish a permanent connection, thereby relieving the hypertension condition.

The connection or "shunt" can relieve symptoms and extend life until a suitable donor liver can be arranged or other measures taken as deemed necessary. TIPS procedures, although minimally invasive, are generally performed in an interventional radiology suite using high doses of fluoroscopy and contrast agents. Furthermore, TIPS procedures and can take an extended period of time, as the procedure is essentially "blind", and includes minimal possibilities to accurately direct the TIPS needle to the correct location.

The Colapinto needles used to perform TIPS procedures have two degrees of freedom, namely a cranial-caudal sliding motion and an axial rotation of the needle about its long axis. The puncture needle may be extended some distance from the end of the Colapinto needle, adding a third degree of freedom. TIPS procedures can be demanding in that the needle trajectories are often incorrect. Frequently, multiple needle passes may be made, which can take an extended amount of time even with experienced physicians. In some cases, it may not be possible to establish the shunt. Furthermore, X-ray use (e.g., from fluoroscopy devices) can cause a large radiation dose to both patients and physicians. Large doses of contrast agent may also be delivered to the patient during TIPS procedures, which may interfere with kidney function and have other side effects. Such procedures may also use significant hospital resources and be costly.

Accordingly, a need exists for systems, methods and devices for TIPS procedures that eliminate or minimize doses of harmful radiation and/or contrast agents as well as improve the accuracy of these procedures and reduce the time required to perform such procedures.

SUMMARY OF THE INVENTION

The invention solves these and other problems in the art by providing methods, systems and devices for image-guided transjugular intrahepatic portosystemic shunt (TIPS) procedures. In some embodiments, the invention relates to instrumentation and methods for accurately targeting the portal vessel during TIPS procedures using electromagnetic tracking techniques.

In some embodiments, the devices, methods, and systems of the invention for performing transjugular intrahepatic portosystemic shunts (TIPS) procedures utilize a position sensor to determine the location and trajectory of a puncture needle.

In some embodiments, the invention includes a device for performing TIPS procedures that includes a position indicating element that is embedded to or attached to a puncture needle used to establish communication between hepatic and portal veins in a patient's liver.

In some embodiments, the invention includes a system for performing image-guided (TIPS) procedures. The system may include a computer element, a tracking device, an imaging device, a needle assembly, and/or other elements.

The computer element may include one or more processors, a memory device, a power source, a control application, one or more software modules, one or more inputs/outputs, a display device, a user input device, and/or other elements. In some embodiments, the one or more processors may be configured to perform one or more of the features and functions of the invention described herein. In some embodiments, the memory device or other memory or data storage elements or methods may store and/or otherwise provide instructions to the one or more processors.

In some embodiments, the tracking device may be operatively connected to the computer element via an input/output or otherwise send and receive data to and from the computer element. In some embodiments, the tracking device may include an electromagnetic tracking device, global positioning system (GPS) enabled tracking device, an ultrasonic tracking device, a fiber-optic tracking device, an optical tracking device, radar tracking device, or other type of tracking device. The tracking device may be used to obtain data regarding the three-dimensional location, position, coordinates, and/or other information regarding one or more position indicating elements within or around an anatomical region of the patient.

In some embodiments, the needle assembly may include a Colapinto needle and a puncture needle. While the needle assembly is described herein as including a "Colapinto needle," a "guide" needle or other elongated hollow instrument having the features ascribed to the "Colapinto" needles referred to herein can be used. In some embodiments, the distal end of the needle body portion of the Colapinto needle may be bent such that the tip is at a 45 degree angle relative to the main axis of the needle body portion. In some embodiments, the angle may more or less than 45 degrees. In some embodiments, the Colapinto needle may be made from a malleable material such that the angle of the bend may be customizable by a physician or other operator. In some embodiments, the bend may be gradual, forming a curve in the distal end/tip of the needle body portion. The puncture needle may be formed using manufacturing techniques and materials so that it is able to exit the distal end of the Colapinto needle. In some embodiments, the portion of the puncture needle extended outside of the Colapinto needle may, at least initially, exit along a path proceeding in a direction tangential to the tip of the Colapinto needle.

In some embodiments, the puncture needle may be formed using a shape memory alloy such as, for example, Nitinol which may be processed so as to be straight in the superelastic state, such that the puncture needle, as it exits the tip of the Colapinto needle, follows its prescribed path (i.e. tangential to the curve of the Colapinto needle).

In some embodiments, the puncture needle may include one or more position indicating elements that may provide position sensor space data regarding the distal end or tip of the puncture needle. In some embodiments, the Colapinto needle may also include one or more position indicating elements that may provide position sensor space data regarding the distal end or tip (or other portion) of the Colapinto needle. In some embodiments, one or more cannulas, needles, catheters, and/or instruments inserted into the Colapinto needle may include one or more position indicating elements that may provide position sensor space data regarding the distal end or tip (or other portion) of the cannula, needle, catheter or other instrument.

In some embodiments, the invention includes a method for utilizing a system for performing image-guided TIPS procedures that involves determining a digital map of the portal vein or other "target vessel" of the patient. The portal vein map may be created using images of the patient's anatomy. The portal vein map may be established using imaging systems and techniques to determine/establish the 3D pathway of a target vessel (e.g., the portal vein). This imaging may include performing a CTA (Computerized tomographic angiography) study, an MRA (Magnetic Resonance Angiogram) study, Rotational fluoroscopic angiographic determination, calibrated biplane angiogram, ultrasound survey of the portal vein, and/or other imaging modalities. The object of the imaging is to determine (e.g., by segmentation) the geometric path of the portal vein and its relevant tributaries. In some embodiments, imaging of the anatomy of the patient may include injecting a contrast agent into the portal system of the patient. A scan may then be performed by an imaging modality to acquire images of the portal system and surrounding anatomy. The resultant images may then be examined.

Using either an automated or manual technique, the geometric pathway of the portal vein is then determined/established and its coordinates recorded in the coordinate system of the images (i.e. "image space"). In some embodiments, smoothing and other geometric operations may be performed to assist with this process. In some embodiments, this portal vein mapping procedure (i.e., imaging and determining pathway of portal vein and/or other operations) may be performed prior to insertion of a TIPS needle assembly into the anatomy of the patient.

In some embodiments, a portal vein map may also be established using intra-procedural ultrasound, such that the geometric pathway of the portal vein (or other target vessel) need not be determined using images of the anatomy of the patient acquired prior to insertion of the needle assembly.

At the time of inserting a needle assembly for performance of the TIPS intervention, a position sensor/tracking device such as, for example, an electromagnetic tracking device, GPS device, fiber optic tracking device, optical tracking or other tracking device system is set up near the patient. The needle assembly may then be introduced into the anatomy of the patient (for TIPS procedures, the needle assembly will be introduced to the patients vascular system and routed into the hepatic vein).

The image space information of the previously obtained images may then be registered to position sensor space information regarding the patient. The two coordinate systems are registered using one or more commonly known registration techniques such as, for example, paired point matching, path matching, ultrasound matching, or other registration techniques. For example, paired point registration may be performed using techniques such as, for example, fiducial based matching in which natural or artificially applied fiducials visible in image space are located in image space, are also identified in position sensor space (e.g., using a probe having one or more position indicating elements associated with the tracking device). Once the locations of at least three fiducials are located in position sensor space and image space, a transformation matrix may be calculated to relate image information of the anatomy of the patient to the coordinate system of the tracking device.

If the pathway of the target vessel is determined using a tracked, calibrated ultrasound, then no registration operations are required, as the vessel path is automatically co-registered with the patient and the path is known in position sensor space.

Following registration (if required), the Colapinto needle is then introduced into the hepatic vein. The initial placement of the Colapinto needle into the hepatic vein may be established in the conventional manner for TIPS procedures, using one or more of various imaging devices such as, for example, ultrasound to establish initial access to the jugular vein and subsequently the hepatic vein. The same catheters and sheaths that are used in the conventional access systems may be applied in the same manner up to the point where the Colapinto needle is placed into the hepatic vein of the liver. This may also involve the use of fluoroscopy as the needle is advanced into the vein.

The tracked puncture needle may then be introduced into the Colapinto needle (e.g., via a port located at the proximal end of the Colapinto needle) and placed into a position such that the tip of the puncture needle is flush with the tip of the Colapinto needle. In embodiments where the puncture needle is solid, a catheter may be introduced into the Colapinto needle along with the puncture needle.

As described herein, one or more position indicating elements of the puncture needle and may send position and/or orientation data to the computer element of the system. Thus, data regarding the position and/or orientation of the position indicating element of the puncture needle are relayed to the computer element. The computer element may use this data to display the current location/position of the instruments relative to the anatomy of the patient (including, for example, the previously mapped portal vein and/or other vessels or organs) onto a display device visible to the physician performing the procedure. The computer element may further calculate potential future paths of one or more instruments (including the puncture needle, a catheter, and/or the Colapinto needle) by projecting ahead where the instruments may go if one or more of the instruments continue in the same direction. The display may indicate to the physician performing the procedure if the current location and trajectory of the puncture needle will result in a "hit" at a point on the portal vein prior to actually extending the puncture needle and testing for blood return.

Because the puncture needle is tracked at its tip and its location and trajectory are known, the physician performing the procedure may determine if the puncture needle will correctly hit the portal vein by simulating what would happen if the physician extended the puncture needle from the Colapinto needle through the wall of the hepatic vein and into the liver parenchyma. During this operation, the path/trajectory of the puncture needle may be continually observed on the display and potentially adjusted during extension (e.g., by twisting, rotating, or translating the needle or activating an internal steering mechanism, etc.). If the physician performing the TIPS procedure determines that the puncture needle will not cross the portal vein, the physician may then readjust the housing of the Colapinto needle by, for example, twisting, extending, retracting or otherwise manipulating the housing until it is determined that the puncture needle will cross the portal vein. The physician may also elect not to extend the needle at all should the physician determine that there is no possibility that a shunt can be correctly established.

Once blood communication is established, a stent may then ultimately be placed and deployed to bridge the portal and hepatic veins.

The various objects, features, and advantages of the invention will be apparent through the detailed description and the drawings attached hereto. It is also to be understood that the following detailed description is exemplary and not restrictive of the scope of the invention.

BRIEF DESCRIPTION OF THE DRAWINGS

FIGS. 3A-3C illustrate examples the distal tip of a puncture needle for use in image-guided TIPS procedures, according to various embodiments of the invention.

DETAILED DESCRIPTION OF PREFERRED EMBODIMENTS

The invention provides devices, systems and methods for assisting or performing image-guided transjugular intrahepatic portosystemic shunt (TIPS) procedures.

Figure 1:
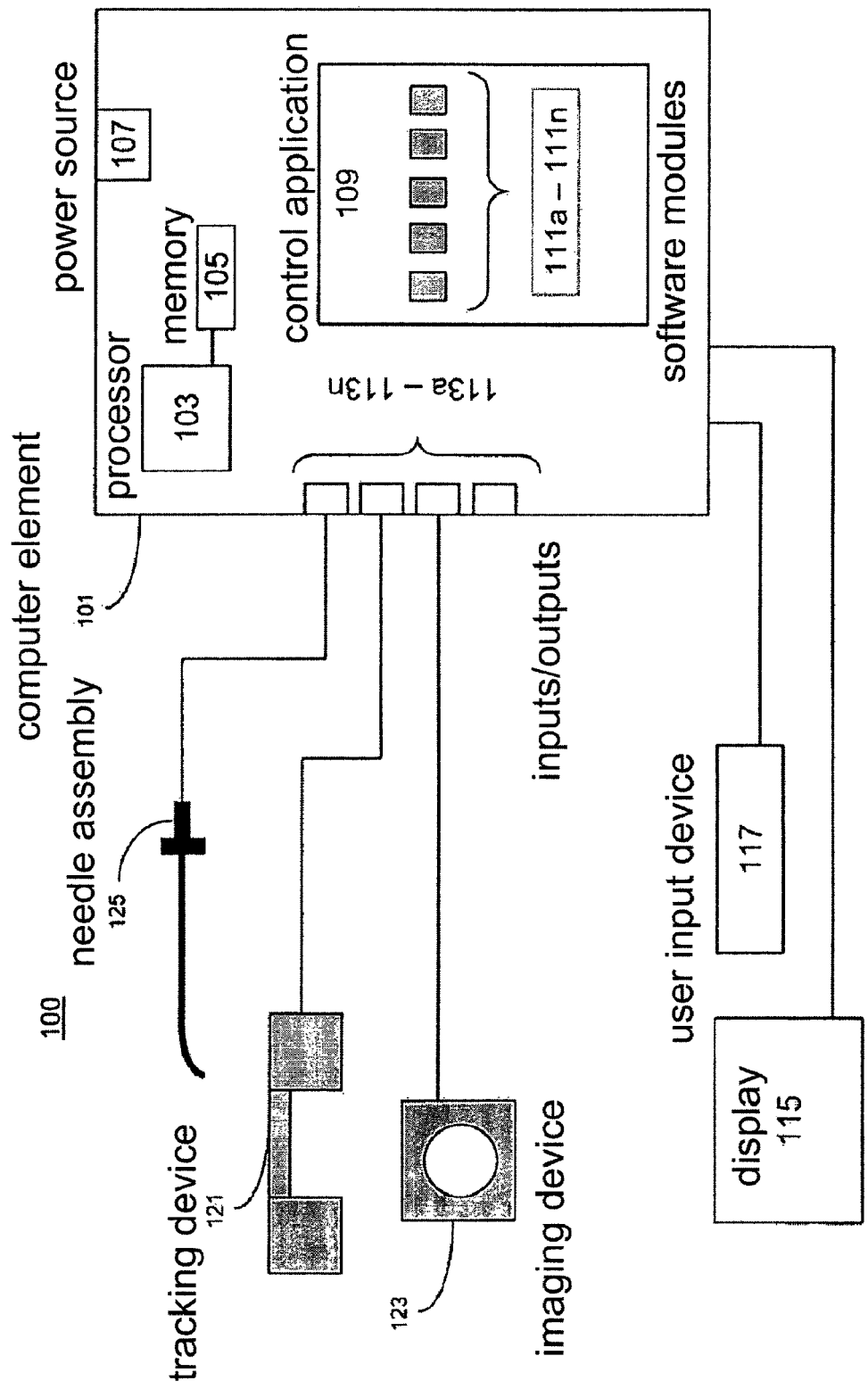
FIG. 1 illustrates an example of an integrated system for image-guided TIPS procedures, according to various embodiments of the invention.

FIG. 1 illustrates a system 100, which is an example of a system for assisting or performing image-guided TIPS procedures. System 100 may include a computer element 101, a tracking device 121, an imaging device 123, a needle assembly 125, and/or other elements.

Computer element 101 may include one or more processors 103, a memory device 105, a power source 107, a control application 109, one or more software modules 111a-111n, one or more inputs/outputs 113a-113n, a display device 115, a user input device 117, and/or other elements. In some embodiments, the one or more processors 103 may be configured to perform one or more of the features and functions of the invention described herein. In some embodiments, memory device 105 or other memory or data storage elements or methods may store data and/or otherwise provide instructions to one or more processors 103.

Computer element 101 may be or include one or more servers, personal computers, laptop computers, mobile computers, or other computer devices. In some embodiments, computer element 101 may receive, send, store, and/or manipulate data necessary to perform any of the processes, calculations, image formatting, image display, or other operations described herein. In some embodiments, computer element 101 may also perform any processes, calculations, or operations necessary for the function of the devices, elements, instruments, or apparatus described herein.

In some embodiments, computer element 101 may host a control application 109. Control application 109 may comprise a computer application which may enable one or more software modules 111a-111n. One or more software modules 111a-111n may enable processor 103 to receive (e.g., via a data reception module), send, and/or manipulate data regarding the anatomy of a patient, one or more objects and/or other data. This data may be stored in memory device 105 or other data storage location. In some embodiments, one or more software modules 111a-111n may also enable processor 103 to receive data (e.g., via the data reception module), send, and/or manipulate data regarding the location, position, orientation, and/or coordinates of one or more position indicating elements (e.g., sensor coils or other position indicating elements). This data may be stored in memory device 105 or other data storage location.

In some embodiments, one or more software modules 111a-111n such as, for example, a display module, may enable processor 103 to produce, format, and/or reformat one or more images from image space data, position/orientation/location data, and/or other data. In some embodiments, images produced from image space data, position/orientation/location data, other data, or any combination thereof may be displayed on display device 115. In some embodiments, one or more software modules 111a-111n such as, for example, the display module, may enable the generation and display of images of the anatomy of the patient with the position and/or orientation of a tracked instrument (e.g., any instrument having one or more position indicating elements thereupon) superimposed thereon in real time (such that motion of the tracked instrument within the anatomy of the patient is indicated on the superimposed images) for use in an image-guided procedure. In some embodiments, one or more software modules 111a-111n such as, for example a display module, may enable processor 103 to produce one or more markings, lines, circles, spheres, letters, numbers or other indicators on one or more images of the anatomy of a patient. In some embodiments, one or more modules 111a-111n such as, for example, a mapping module, may enable processor 103 to map a target vessel (e.g., a portal vein) or other portion of a patient's anatomy and/or to perform other operations related to a map of the target vessel or portion of the patient's anatomy. In some embodiments, one or more modules 111a-111n such as, for example, display module may generate and display (e.g., on display device 115) the position of a puncture needle relative to a target vessel, a projected path of the puncture needle including a path of the puncture needle will follow if the puncture needle is extended past a distal end portion of the guide needle, a point at which the puncture needle will intersect the target vessel if the projected path of the puncture needle intersects the determined path of the target vessel, and an indicator of the closest approach from the puncture needle to the target vessel if the projected path of the puncture needle does not intersect the determined path of the target vessel.

In some embodiments, display device 115 may include a computer monitor or other visual display device such as, for example, an LCD display, plasma screen display, cathode ray tube display, or other display device. In some embodiments, input device 117 may include one or more of a mouse, a stylus, a keyboard, a touchscreen interface (which may be associated with or integrated with display device 115), a voice activated input device (including a microphone and associated voice processing software) and/or other device wherein a user (e.g., a physician performing a TIPS procedure or assistant thereto) can provide input to system 100 or its components.

In some embodiments, tracking device 121 may be operatively connected to computer element 101 via an input/output 113. In some embodiments, tracking device 121 need not be directly operatively connected to computer element 101, but data may be sent and received between tracking device 121 and computer element 101. Tracking device 121 may include an electromagnetic tracking device, global positioning system (GPS) enabled tracking device, an ultrasonic tracking device, a fiber-optic tracking device, an optical tracking device, radar tracking device, or other type of tracking device. Tracking device 121 may be used to obtain data regarding the three-dimensional location, position, coordinates, and/or other information regarding one or more position indicating elements within or around an anatomical region of the patient. Tracking device 121 may provide this data/information to computer element 101. In some embodiments, the position indicating elements tracked by tracking device 121, may be placed on or integrated in needle assembly 125, and/or other elements.

In some embodiments, imaging device 123 may include may include x-ray equipment, computerized tomography (CT) equipment, positron emission tomography (PET) equipment, magnetic resonance imaging (MRI) equipment, fluoroscopy equipment, ultrasound equipment, an isocentric fluoroscopic device, a rotational fluoroscopic reconstruction system, a multislice computerized tomography device, an intravascular ultrasound imager, an optical coherence tomography (OCT) device, an optical imaging device, a single photon emission computed tomography device, a magnetic resonance imaging device, or other imaging/scanning equipment.

Figure 2A:
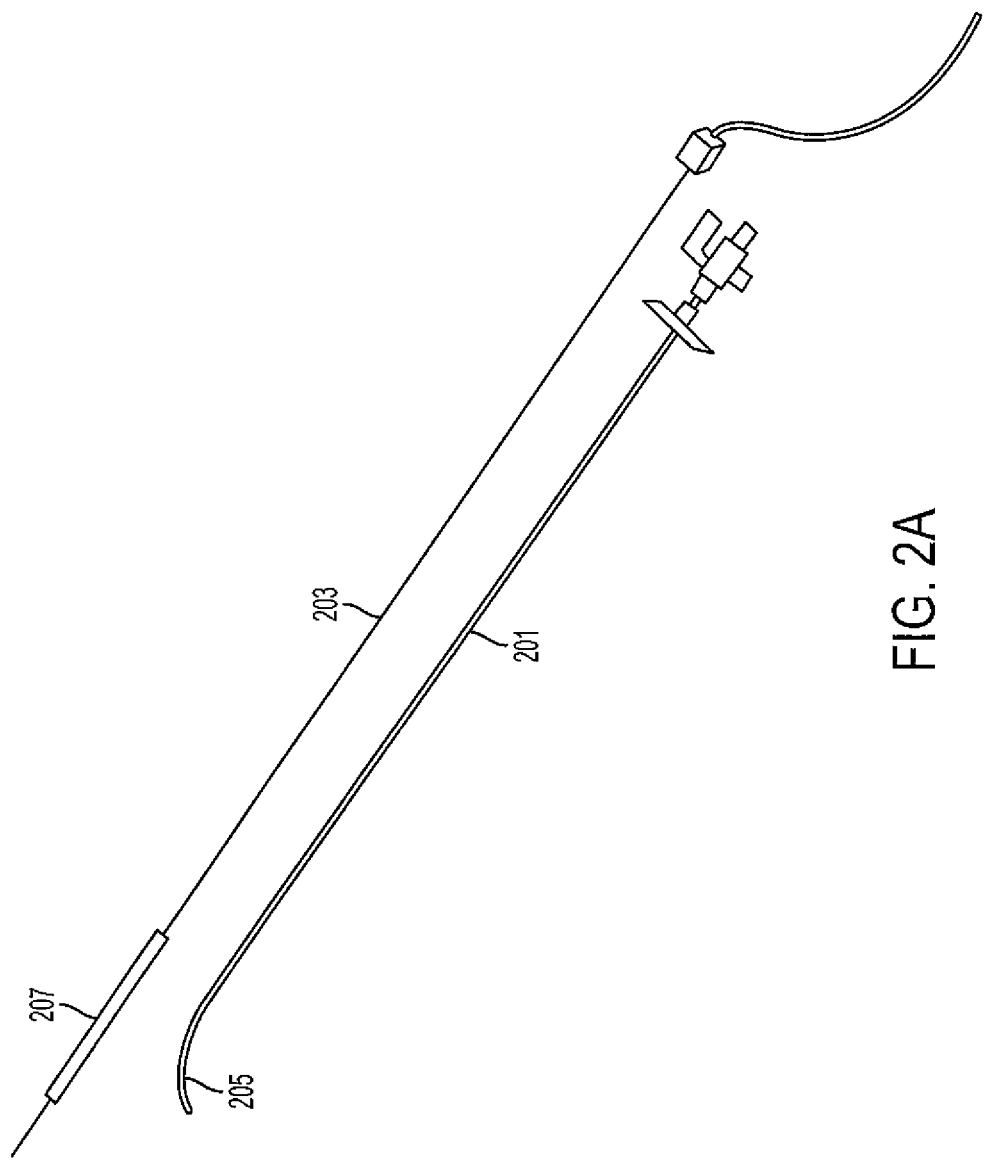
FIGS. 2A and 2B illustrate examples of Colapinto and puncture needles for use in image guided TIPS procedures, according to various embodiments of the invention.

In some embodiments, needle assembly 125 may include a Colapinto needle and a puncture needle. While needle assembly 125 is described herein as including a "Colapinto needle," a "guide" needle or other elongated hollow instrument having the features ascribed to the "Colapinto needles" referred to herein can be used. FIG. 2A illustrates a separated needle assembly, which may include a Colapinto needle 201 and a puncture needle 203. Colapinto needle 201 may include a standard Colapinto needle having an elongated needle body portion that is hollow along its length (or that otherwise includes a lumen). In some embodiments the Colapinto needle may be referred to as a guide needle. In some embodiments, the needle body portion of Colapinto needle 201 may be, for example, 60 cm long with a 16 gauge (16 G) diameter. Other lengths and/or diameters may be used. In some embodiments, a portion of the distal end/tip (e.g., the distal 5 cm) of the needle body portion of Colapinto needle 201 may be bent. For example, in some embodiments, the distal end of the needle body portion of Colapinto needle 201 may be bent such that the tip is at a 45 degree angle relative to the main axis of the needle body portion. In some embodiments, the angle may more or less than 45 degrees. In some embodiments, Colapinto needle 201 may be made from a malleable material such that the angle of the bend may be customizable by a physician or other operator. In some embodiments, the bend may be gradual, forming a curve in the distal end/tip of the needle body portion. In some embodiments, Colapinto needle 201 may include other elements, such as, for example, elements at the proximal end of the needle body portion (e.g., a hub, a valve, or a port for introducing catheters or other needles into the hollow body of Colapinto needle 201, and/or other elements).

Figure 2B:
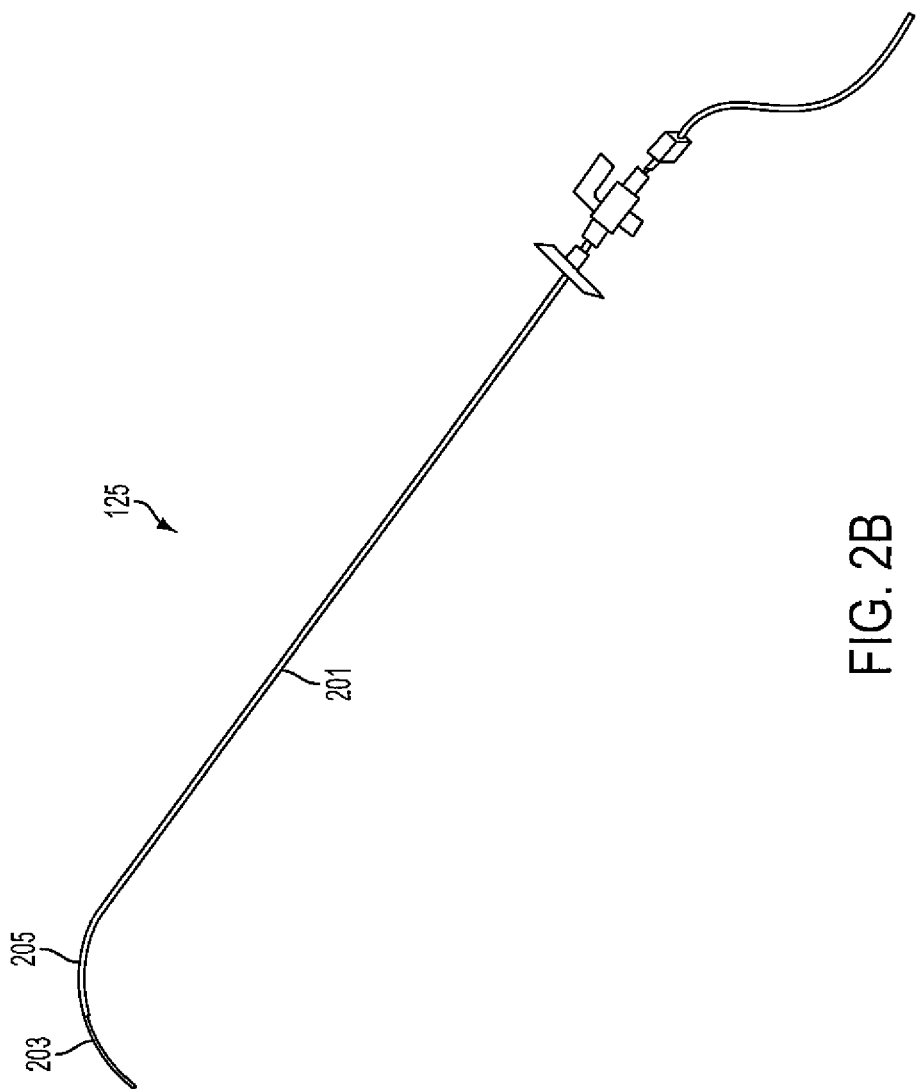

In some embodiments, puncture needle 203 may also include an elongated needle body portion, sized to slidably fit within the hollow body of Colapinto needle 201. In some embodiments, as described herein, puncture needle 203 may be hollow or otherwise have a lumen running the length thereof. In some embodiments, puncture needle 203 may be solid and/or may accommodate a catheter or other lumen bearing device around its outer surface. In some embodiments, the needle body portion of puncture needle 203 may, for example, be 65 cm long and may have an 18 gauge (18 G) diameter. FIG. 2B illustrates needle assembly 125 including Colapinto needle 201 assembled with puncture needle 203, wherein puncture needle 203 is deployed and extends out of Colapinto needle 201.

Puncture needle 203 may be formed using manufacturing techniques and materials so that as it exits the distal end 205 of Colapinto needle 201. In some embodiments, the portion of puncture needle 203 extended outside of Colapinto needle 201 may, at least initially, exit along a path proceeding in a direction tangential to tip 205 (or distal end 205) of Colapinto needle 201. In some embodiments, this may be accomplished by employing a spring element near the tip of puncture needle 203 that ensures the direction is maintained as tangential to the curve of the Colapinto needle. For example, section 207 of puncture needle 203 may include or be constructed of a spring element welded proximally to a wire or tube and distally to a sharp tip. In some embodiments, puncture needle 203 may be formed using a shape memory alloy such as, for example, Nitinol which may be processed so as to be straight in the super-elastic state, such that puncture needle 203, as it exits the tip 205 of Colapinto needle 201, follows its prescribed path (i.e. tangential to the curve of Colapinto needle 201). Nitinol has the advantage of being relatively kink resistant enabling it to be bent to extreme angles with no effect to the integrity of the tube or wire formed from it. Also, when annealed into its super-elastic condition and formed into a straight shape, it will not plastically deform, but will always return to its straight shape, even when tortuously bent. This provides a needle that when contained within a cannula, will always exit tangent to the slope end of the cannula. Therefore, if puncture needle 203 is made using properly treated Nitinol and is contained with Colapinto needle 201, the tip of puncture needle 203 will always exit in the direction of the distal tip of Colapinto needle 201 and not undertake any deflection caused by the bent tip of Colapinto needle 201 (as might another material). This may assist in performing a TIPS procedure, as it may not be possible to predict the path of puncture needle 203 should it be susceptible to bending as it exits the distal tip of Colapinto needle 201.

Figure 3B:
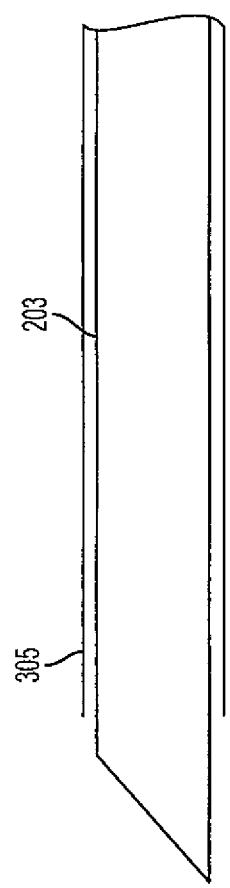

In some embodiments, puncture needle 203 may include one or more position indicating elements that may provide position sensor space data regarding the distal end or tip of puncture needle 203. FIG. 3A illustrates an enlarged view of a tip portion of puncture needle 203 having a position indicating element 301, which may be a wire coil or other element that provides position and orientation of the tip portion of puncture needle 203 in position sensor space in concert with a tracking device (e.g., tracking device 121). Puncture needle 203 may also include lead wires 303 extending from position indicating elements 301 up the length of puncture needle 203.

In some embodiments, Colapinto needle 201 may also include one or more position indicating elements that may provide position sensor space data regarding the distal end or tip (or other portion) of Colapinto needle 201. In some embodiments, one or more cannulas, needles, catheters, and/or instruments inserted into Colapinto needle 201 may include one or more position indicating elements that may provide position sensor space data regarding the distal end or tip (or other portion) of the cannula, needle, catheter or other instrument.

In embodiments, wherein puncture needle 203 is solid, a hollow cannula or catheter may be placed over puncture needle 203 so that a conduit for blood flow is provided. For example, if a solid puncture needle sheathed by a catheter is used to perform a TIPS procedure and thereby bridge the portal vein and the hepatic vein, the solid puncture needle portion may be extracted from the assembly, thereby leaving only the catheter which enables a test for blood return. If blood is returned a successful traversal of the portal vein is confirmed. As such, In some embodiments, puncture needle 203 may be shrouded by a catheter in the same way as a Rösch-Uchida system (see e.g., FIG. 3B wherein a catheter 305 shrouds puncture needle 203). In such systems, a position indicating element may be wound around the outside of a puncture needle or catheter. In some embodiments, puncture needle 203 may be formed by, for example, welding or shaping a sharp tip onto a hollow tube portion. In such cases, a position indicating element may be placed inside the distal portion of the hollow tube portion adjacent to the sharp tip. Any lead wires associated with the position indicating element may run through the interior of the hollow tube portion and may be transitioned to the exterior, if appropriate.

Figure 3C:
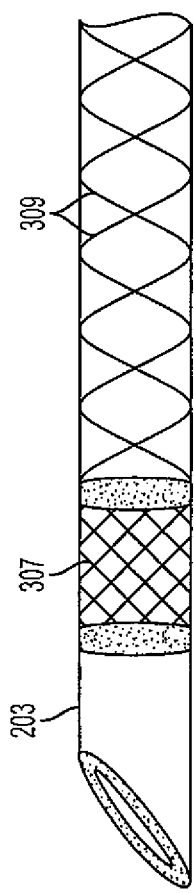

In some embodiments, puncture needle 203 may be hollow, therefore enabling blood flow therethrough. In instances wherein a hollow puncture needle is used, a position indicating element may be wound around the outside of a hollow puncture needle or attached adjacent to the needle. FIG. 3C illustrates puncture needle 203, wherein the wire comprising position indicating element 307 is wound around the outside of needle 203, with lead wires 309 also wound around the outside of needle 203 to connection points elsewhere in the system. The use of a hollow puncture needle, allows a user to dispense with the use of a separate cannula or catheter, as blood (or other fluid) may be drawn directly up the hollow interior of the puncture needle. In some embodiments, a hollow puncture needle may be constructed of a hollow spring material such that the lead wires (e.g., lead wires 309) of position indicating element 307 may run along the needle's length. In some embodiments, the puncture needle may include an exterior wound coil with leadwires either communicated to the inside of the needle at a convenient point or run along the outside of the needle. In an embodiment where the leadwires run along the outside of the needle, a protective coating such as a heatshrink, pyralene, or other coating may be applied.

Figure 4A:
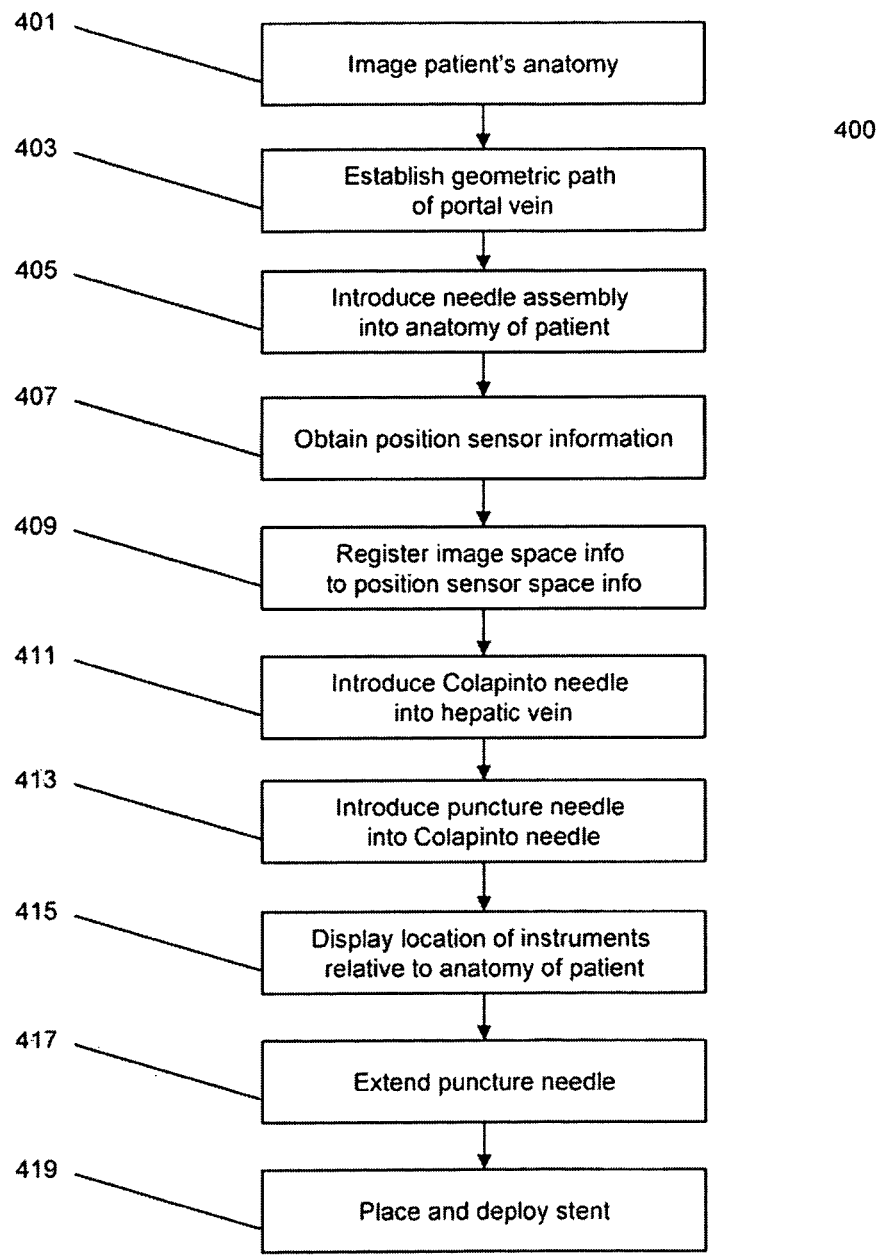
FIG. 4A illustrates an example of a process for image-guided TIPS procedures, according to various embodiments of the invention.

In some embodiments, an image guided TIPS procedure may be assisted/performed on a patient using the systems of the invention such as, for example, system 100 or parts thereof. FIG. 4A illustrates a process 400, which is an example of a process for assisting/performing an image-guided TIPS procedure. In some embodiments, an image guided TIPS procedure may utilize a digital map of the portal vein or other "target vessel" of the patient. A portal vein map may be created using images of the patient's anatomy. As such, process 400 may include an operation 401, wherein one or more images or image scans of the patient are obtained. In some embodiments, one or more modules 111a-111n of computer element 101 (e.g., a data reception module) may enable computer element 101 to receive the one or more images, images scans and/or other image data. The portal vein map may be established using imaging systems (e.g., imaging device 123) and techniques to determine/establish the 3D pathway of a target vessel (e.g., the portal vein). This imaging may include performing a CTA (Computerized tomographic angiography) study, an MRA (Magnetic Resonance Angiogram) study, Rotational fluoroscopic angiographic determination, calibrated biplane angiogram, ultrasound survey of the portal vein, and/or other imaging modalities. The object of the imaging is to determine (e.g., by segmentation) the geometric path of the portal vein and its relevant tributaries. In some embodiments, imaging of the anatomy of the patient may include injecting a contrast agent into the portal system of the patient. A scan may then be performed by an imaging modality (e.g., imaging device 123) to acquire images of the portal system and surrounding anatomy. The resultant images may then be examined.

In an operation 403, using either an automated or manual technique, the geometric pathway of the portal vein is then determined/established and its coordinates recorded in the coordinate system of the images (i.e. "image space"). In some embodiments, smoothing and other geometric operations may be performed to assist with this process. In some embodiments, this portal vein mapping procedure (i.e., imaging and determining pathway of portal vein and/or other operations) may be performed prior to insertion of TIPS needle assembly 125 into the anatomy of the patient.

Figure 4B:
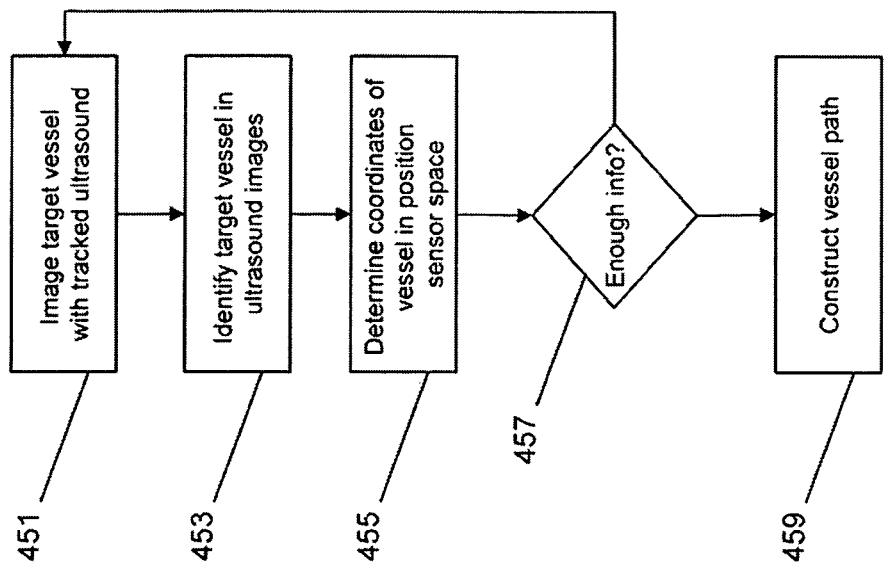
FIG. 4B illustrates an example of a process for constructing a 3D path of a target vessel using a tracked, calibrated ultrasound, according to various embodiments of the invention.

In some embodiments, a portal vein map may also be established using intra-procedural ultrasound, such that the geometric pathway of the portal vein (or other target vessel) need not be determined using images of the anatomy of the patient acquired prior to insertion of needle assembly 125. FIG. 4B illustrates a process 450, whereby a tracked and calibrated ultrasound may be used to establish a three dimensional map of the portal vein (or other target vessel). A "tracked" ultrasound transducer refers to an ultrasound transducer fitted with a position indicating element whose position and orientation can be determined in position sensor space by a tracking system (e.g., tracking system 121). The term "calibrated" ultrasound transducer refers to an ultrasound transducer that is pre-calibrated in a medium simulating human tissue (or otherwise calibrated) so that a location in the 2D image plane of the transducer, when combined with the spatial location and orientation of the transducer's imaging plane (known due to the position indicating elements) provides enough information to determine the spatial location in position sensor space of any point within the scan plane. As such, if a location appears at a point u, v (wherein "u," and "v" correspond to the "x" and "y" location of a point in the coordinate system of the scan plane) in the image plane of the ultrasound and the orientation and location of the ultrasound transducer is known in position sensor space, this information may be combined to determine the location (u, v) in position, sensor space.

Process 450 includes an operation 451, wherein the tracked and calibrated ultrasound is used to obtain an image of a portion of the patient's anatomy wherein the portal vein (or other target vessel) is located. In an operation 453, the portal vein's (or other target vessel) location within the image is identified either manually or using an automated technique. Operation 453 may include determining the "ultrasound coordinates" (u, v) of the portal vein within the scan plane of the ultrasound transducer. In an operation 455, the X, Y, Z, position of the identified portion of the portal vein (or other target vessel) within the scan plane of the ultrasound will be determined in position sensor space. This can be determined by virtue of the position indicating element in the ultrasound transducer wherein the ultrasound coordinates (u, v) together with the calibration information may then be converted to position sensor space coordinates. In an operation 457, it is determined whether enough information regarding the portal vein (or other target vessel) has been obtained. If not, process 450 returns to operation 451 to obtain images of additional portions of the portal vein (or other target vessel), which are then visualized and their coordinates in position sensor space are determined. If enough information has been obtained, process 450 proceeds to an operation 459, wherein this information is used to construct a full 3D position sensor space representation of the path of the portal vein (or other target vessel). For additional information regarding tracked ultrasound, see U.S. Patent Application Publication No. 20070167787 (U.S. patent application Ser. No. 11/471,629), entitled "Device and Method for Trackable Ultrasound," which is hereby incorporated by reference herein in its entirety.

No matter the method used to determine the path of the target vessel, it may be desirable to segment the path of the target vessel and identify/determine specific points in/on the vessel such as, for example, points forming the centerline of the vessel. Furthermore, the path may be established as a series of coordinates such that the spatial coordinates of the target vessel are known in image space (e.g., when using preoperative imaging) or position sensor space (e.g., when using intraoperative imaging). The path may comprise, for example, a series of points smoothed or linked by a piecewise linear or bicubic spline. If the spatial coordinates of the target vessel are initially known in image space, a subsequent registration with position sensor space coordinates establishes the path of the vessel in patient space, where all other measurements take place.

In some embodiments, one or more modules 111a-111n of computer element 101 (e.g., a mapping module) may be used by computer element 101 to assist and/or perform the operations discussed herein regarding creating a map of the portal vein or other portion of the anatomy of the patient such as, for example, determining the geometric pathway of a target vessel in image space, smoothing or other geometric operations, segmenting a target vessel, determining centerline points of a target vessel, smoothing or linking points by a piecewise bicubic spline, and/or other operations associated with creating a map in image space of a target vessel or other portion of the anatomy of a patient.

At the time of inserting needle assembly 125 for performance of the TIPS intervention, a position sensor/tracking device (e.g., tracking device 121) such as, for example, an electromagnetic tracking device, GPS device, fiber optic tracking device, optical tracking or other tracking device system is set up near the patient. Tracking system 121 enables a computer system (e.g., computer element 101) to determine the location and orientation of position indicating elements (e.g., position indicating elements 301 or 307) such as electromagnetic sensing coils, GPS elements, or other positing indicating elements within the volume of the position sensor. These position indicating elements may be attached to one or more elements of the system as described herein (e.g., on or in puncture needle 203) and/or on or in the anatomy of the patient. Tracking system 121 determines the position and orientation of the position indicating elements within its own coordinate system referred to hereinafter interchangeably as "position sensor space" or "patient space". As such, process 400 may include an operation 405, wherein the needle assembly is introduced into the anatomy of the patient (for TIPS procedures, the needle assembly will be introduced to the patient's vascular system and routed into the hepatic vein). In an operation 407, one or more position indicating elements located within the anatomy of the patient (e.g., via their association with needle assembly 125) may be sampled by the tracking system, thereby obtaining position sensor space information regarding needle assembly and/or portions of the anatomy of the patient. As described herein, other methods/instruments may be used to gather position sensor space information regarding the anatomy of the patient.

In an operation 409, the image space information of the images are then registered to the position sensor space information. The two coordinate systems are registered using one or more commonly known registration techniques such as, for example, paired point matching, path matching, ultrasound matching, or other registration techniques. For example, paired point registration may be performed using techniques such as, for example, fiducial based matching in which natural or artificially applied fiducials visible in image space are located in image space, are also identified in position sensor space (e.g., using a probe having one or more position indicating elements associated with tracking system 121). Once the locations of at lease three fiducials are located in position sensor space and image space, a transformation matrix may be calculated to relate image information of the anatomy of the patient to the coordinate system of tracking device 121. Further information regarding registration methods can be found in U.S. Patent Application Publication No. 20050182319 (U.S. patent application Ser. No. 11/059,336) entitled "Method and Apparatus for Registration, Verification, and Referencing of Internal Organs," the entirety of which is hereby incorporated by reference herein. Due to the mobility of the liver, methods that either account for liver motion or preserve the location of the organ from the time of scan to the time of intervention may provide certain advantages. Furthermore, methods including direct tracking or image based correction techniques may also be employed to track the liver motion during the procedure to ensure the portal vein map remains in registration with the position sensor space.

Methods of registration that account for liver motion may be based on intraoperative imaging such as ultrasound or fluoroscopy. Other methods may include direct liver tracking such as, for example, dynamic referencing of the organ using implanted needles, fiducials, transmitters, and/or other elements that can be used to establish/determine a rigid or non-rigid transformation of the liver from the time of the scan. Additional information regarding dynamic referencing methods can be found in U.S. Patent Application Publication No. 20050182319 (U.S. patent application Ser. No. 11/059,336) entitled "Method and Apparatus for Registration, Verification, and Referencing of Internal Organs." Liver tracking and motion accounting modeling techniques may be used to track the organ throughout the procedure.

As discussed herein, in some embodiments, a tracked, calibrated ultrasound transducer may be used to obtain image space information intra-operatively. In this way, the patient space coordinates of the portal vein (or other portions of a patient's anatomy) may be determined directly. As a tracked and calibrated ultrasound transducer is automatically capable of correlating the images it produces into position sensor space, it may not be necessary to register the image information from the tracked ultrasound to the patient space information.

As described herein, the TIPS intervention includes introducing a Colapinto needle into the hepatic vein (or other vessel or area near the target vessel). With regard to process 400, if Colapinto needle 201 has not yet been introduced into the hepatic vein in operation 405, needle assembly 125 is navigated in an operation 411, such that Colapinto needle 201 is introduced into the hepatic vein. The initial placement of Colapinto needle 201 into the hepatic vein may be established in the conventional manner for TIPS procedures, using one or more of various imaging devices such as, for example, ultrasound to establish initial access to the jugular vein and subsequently the hepatic vein. The same catheters and sheaths that are used in the conventional access systems may be applied in the same manner up to the point where Colapinto needle 201 is placed into the hepatic vein of the liver. This may also involve the use of fluoroscopy as the needle is advanced into the vein.

In an operation 413, tracked puncture needle 203 is then introduced into Colapinto needle 201 and placed into a position such that the tips of catheter 305 (if used) and puncture needle 203 are flush with the tip of Colapinto needle 201. In embodiments where puncture needle 203 is solid, catheter 305 may be introduced into Colapinto needle 201 along with puncture needle 203. In some embodiments, various markings on puncture needle 203 and/or spacers placed between a hub of Colapinto needle 201 and a hub of puncture needle 203 may be used to establish the proper location for the tip of puncture needle 203.

As described above, one or more position indicating elements (e.g., position indicating element 301) of puncture needle 203 and tracking system 121 of system 100 are operatively connected to or otherwise send data to computer element 101 of system 100. Thus, data regarding the position and/or orientation of position indicating element 301 (and/or other position indicating elements associated with system 100 positioned within the active volume of the position sensor) are relayed to computer element 101. Computer element 101 may use this data to display (e.g., using a display module) the current location/position of the instruments relative to the anatomy of the patient (including, for example, the previously mapped portal vein and/or other vessels or organs) onto a display device (e.g., display device 115) visible to the physician performing the procedure. Computer element 101 may further calculate (e.g., using a display module) potential future paths of one or more instruments (including puncture needle 203, catheter 205, and/or Colapinto needle 201) by projecting ahead where the instruments may go if one or more of the instruments continue in the same direction. As such, process 400 may include an operation 415, wherein the position and trajectory of puncture needle 203 are generated, projected, and/or displayed on a computer display (e.g., display device 115) onto which the registered images of the portal vein have been loaded. The display indicates to the physician performing the procedure if the current location and trajectory of puncture needle 203 (housed within Colapinto needle 201) will result in a "hit" at a point on the portal vein prior to actually extending puncture needle 203 and testing for blood return.

Because puncture needle 203 is tracked at its tip and its location and trajectory are known, the physician performing the procedure may determine if puncture needle 203 will correctly hit the portal vein. In an operation 417, the physician may extend puncture needle 203 from Colapinto needle through the wall of the hepatic vein and into the liver parenchyma until it hits the portal vein. During this operation, the path/trajectory of puncture needle 203 may be continually observed on the display and potentially adjusted during extension (e.g., by twisting the needle if beveled or activating an internal steering mechanism). If the physician performing the TIPS procedure determines that puncture needle 203 will not cross the portal vein, the physician may then readjust the housing of Colapinto needle 201 by, for example, twisting, extending, retracting or otherwise manipulating the housing until it is determined that puncture needle 201 will cross the portal vein. In some embodiments, operation 417 may be performed robotically.

In an operation 419, a stent may be ultimately placed and deployed to bridge the portal and hepatic veins.

Figure 5:
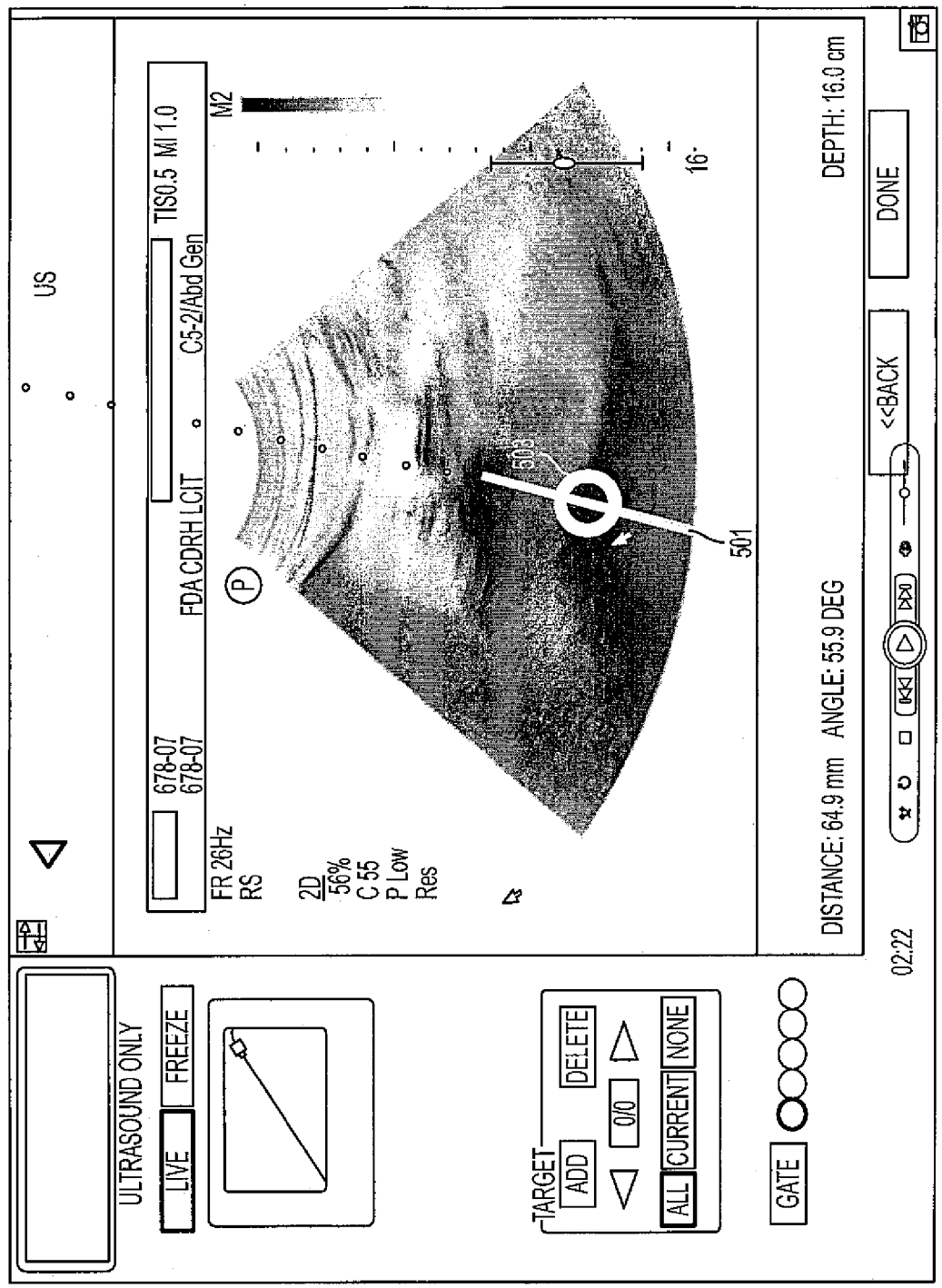
FIG. 5 illustrates an example of a display of a portion of a patient's anatomy, according to various embodiments of the invention.

In some embodiments as discussed herein, the crossing point on the portal vein is imaged using an ultrasound apparatus. Puncture needle 203 and Colapinto needle 201 may then collectively manipulated until the location of the crossing of puncture needle 203 with the scan plane of the ultrasound apparatus is predicted to occur at the location of the vessel. FIG. 5 illustrates a display 500, which is an example of an ultrasound image (i.e., the image captured by the scan plane of an ultrasound transducer used in conjunction with the system of the invention), wherein the crossing point of the puncture needle with the portal vein is visualized as a circle. Line 501 of FIG. 1 illustrates a projection of puncture needle 203 onto the scan plane of the ultrasound. Circle 503 illustrates a point at which the needle is anticipated to cross the scan plane. The portion of line 501 above circle 503 represents a projection of the path of puncture needle 203 as it passes beyond the scan plane. Other representations of puncture needle 203 or other elements of needle assembly 125 may also be displayed.

Typical Colapinto needles generally have only 2 degrees of freedom: a longitudinal motion and a twisting motion. This often makes it difficult to puncture a specific location on a vessel. However, another degree of freedom is actually available, namely, the location of the puncture in the vessel, which is typically somewhat arbitrary. On some scenarios, only a single location of the portal vein may be imaged so the entry point into the portal vein may be constrained. Monitoring multiple points of potential entry of a puncture needle would be advantageous. As such, visualization of and access to a larger portion of a target vessel would be advantageous. In some instances, all potential crossing locations in the portal vein and its tributaries may be monitored by scanning an ultrasound transducer around the anatomy of the patient while imaging the portal vein. However, this scanning of the anatomy may be tedious and difficult to visualize the whole target area. As such, the use of the systems, processes, and features disclosed herein may be used to advantageously enable visualization and access to multiple locations on the portal vein and its branches as valid entry points.

Because a portal vein map has been established, computer element 101 can determine if the current trajectory of puncture needle 203 will come close to or intersect the portal vein's path at any location. The distance between the trajectory and any crossing point may also be determined and displayed to the physician performing the TIPS procedure.

As discussed above, in some embodiments, the path of the portal vein that was determined prior to or during the procedure (e.g., in operation 403) may be displayed on display device 115 along with the trajectory of puncture needle 203. The trajectory of puncture needle 203 is examined by the physician performing the TIPS procedure to determine if it will cross the portal vein. If a crossing location is found, puncture needle 203 may be extended (e.g. in operation 417) until it is calculated to cross from the hepatic vein into the portal vein. Once the crossing has been made, the physician may verify the connection between the veins by examining if blood can be extracted through puncture needle 203 (if hollow) or any hollow cannula or catheter (e.g., catheter 305) that is surrounding puncture needle 203.

Figure 6:
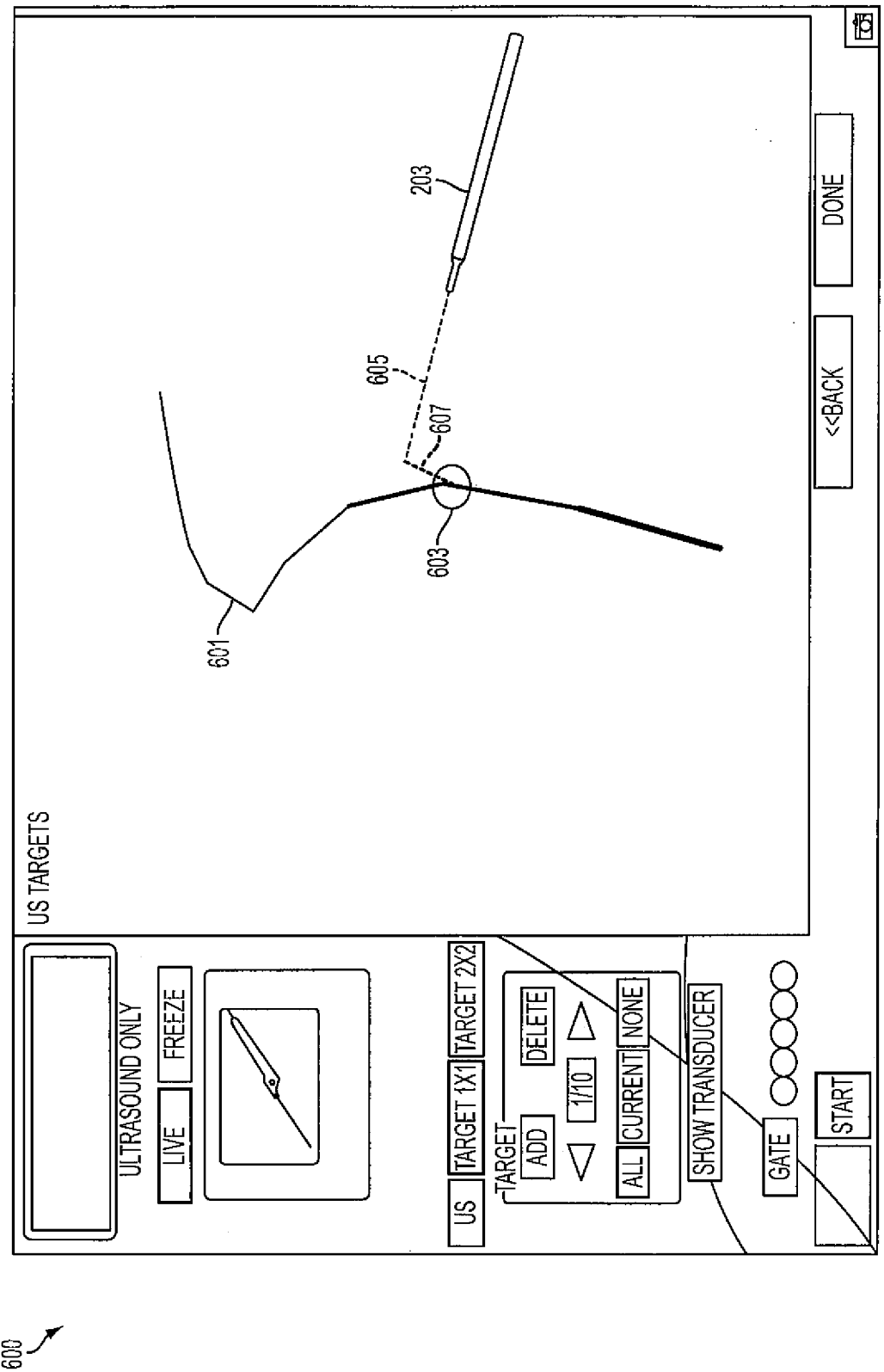
FIG. 6 illustrates an example of a display of a portion of a patient's anatomy including a target vessel relative to a puncture needle, according to various embodiments of the invention.

In some embodiments, in conjunction with displaying the location of puncture needle 203 relative to the mapped portal vein, computer element 101 may calculate the closest approach to the portal vein and display it, along with the distance to the vessel. FIG. 6 illustrates a display 600, which is an example of a display of a representation of the portal vein (or other target vessel) and puncture needle 203. Vessel 601 in display 600 represents the portal vein. Circle 603 represents a predefined distance to the portal vein, e.g., a 2 mm approach. As stated above, item 203 represents the current location of the tip of puncture needle 203. Dotted line 605 represents the trajectory of puncture needle 203. Line 607 represents the closest approach to the portal vein. The example illustrated in display 600 indicates that the current trajectory of puncture needle 203 will not cause the portal vein to be punctured.

Figure 7:
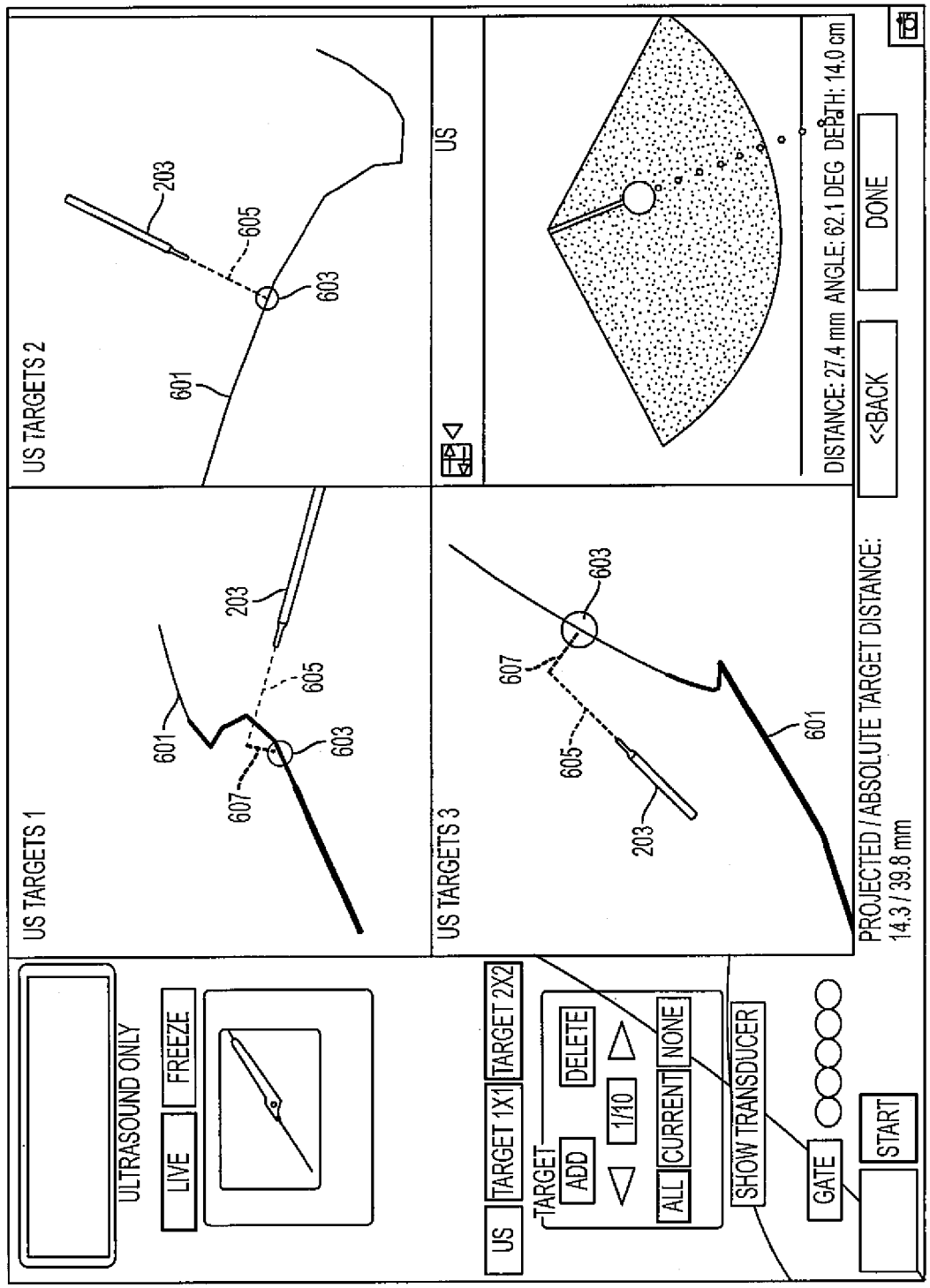
FIG. 7 illustrates an example of a display of a portion of a patient's anatomy including a target vessel relative to a puncture needle, according to various embodiments of the invention.

FIG. 7 illustrates display 700, which illustrates multiple depictions of the information depicted in FIG. 6. Display 700 illustrates puncture needle 203, its location and trajectory relative to the representation 601 of the portal vein on several projected views simultaneously. The bottom right quadrant of the images displayed in FIG. 7 illustrates a live ultrasound view in which progress may be examined. This view is not directly related to the accompanying views of the needle trajectory and vessel path that is shown in the other quadrants of FIG. 7. The circle in the bottom right quadrant illustrates a predicted crossing point of puncture needle 203's trajectory with the live scan plane of an ultrasound. This is calculated as a result of knowledge of puncture needle 203's trajectory from its position indicating element (e.g. position indicating element 301) and the direction of the scan plane that is known in position sensor space due to one or more position indicating elements associated with the ultrasound transducer. Information from these position indicating elements is used with calibration information of the tracked ultrasound and image information to generate and display the location of puncture needle's crossing point with the scan plane. The solid line represents a projection of puncture needle 203 introduced out of the scan plane, while the dotted line represents a predicted trajectory of puncture needle 203 (again, out of the scan plane) after its crossing point with the scan plane. When puncture needle actually crosses the scan plane, a live ultrasound echo of the portion of puncture needle 203 intersecting the scan plane will be displayed in the lower right quadrant image.

The projected and absolute target distances that are shown in the lower left portion of display 700 show the distance from the projected closest approach and current puncture needle tip to the closest approach to the portal vein. The projected target distance shows how close the needle tip will come on its current trajectory (i.e., 14.3 mm in the example of FIG. 7). The physician performing the TIPS procedure must then manipulate puncture needle 203 until the projected target distance (i.e., the first number) is zero and then advance with puncture needle 203 until the absolute target distance (i.e., the second number) of the tip to the portal vein is also zero. At that time, the tip of puncture needle 203 and the portal vessel will have crossed.

Figure 8:
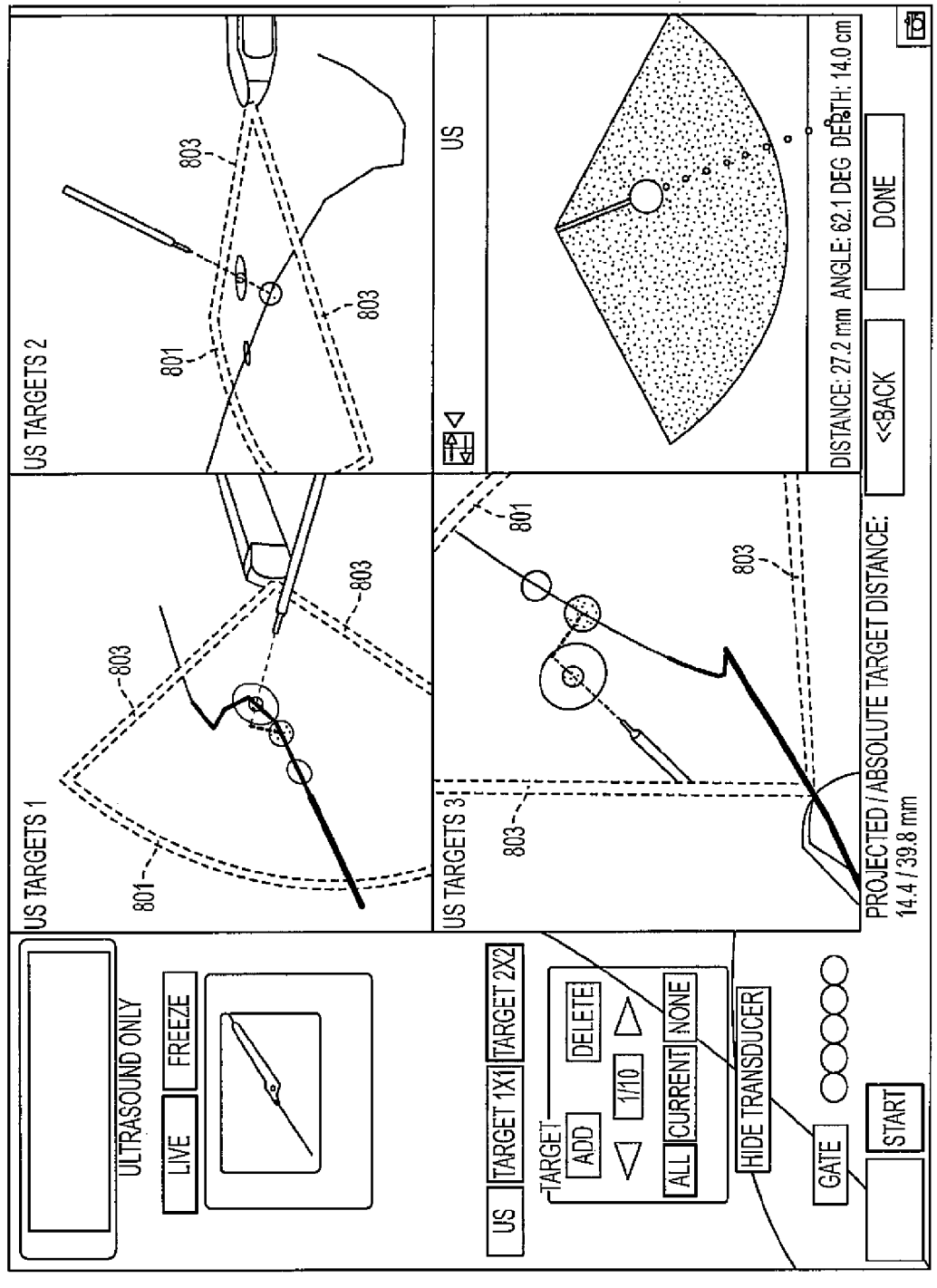
FIG. 8 illustrates an example of a display of a portion of a patient's, anatomy including a target vessel relative to a puncture needle, according to various embodiments of the invention.

FIG. 8 illustrates display 800, which is an example of a comprehensive view of the information displayed in FIGS. 6 and 7, and which illustrates the scan plane of a tracked and calibrated ultrasound transducer (if used) and what the ultrasound transducer is showing. Arch 801 and its associated legs 803 indicate the ultrasound transducer's imaging plane or "scan plane."

Figure 9:
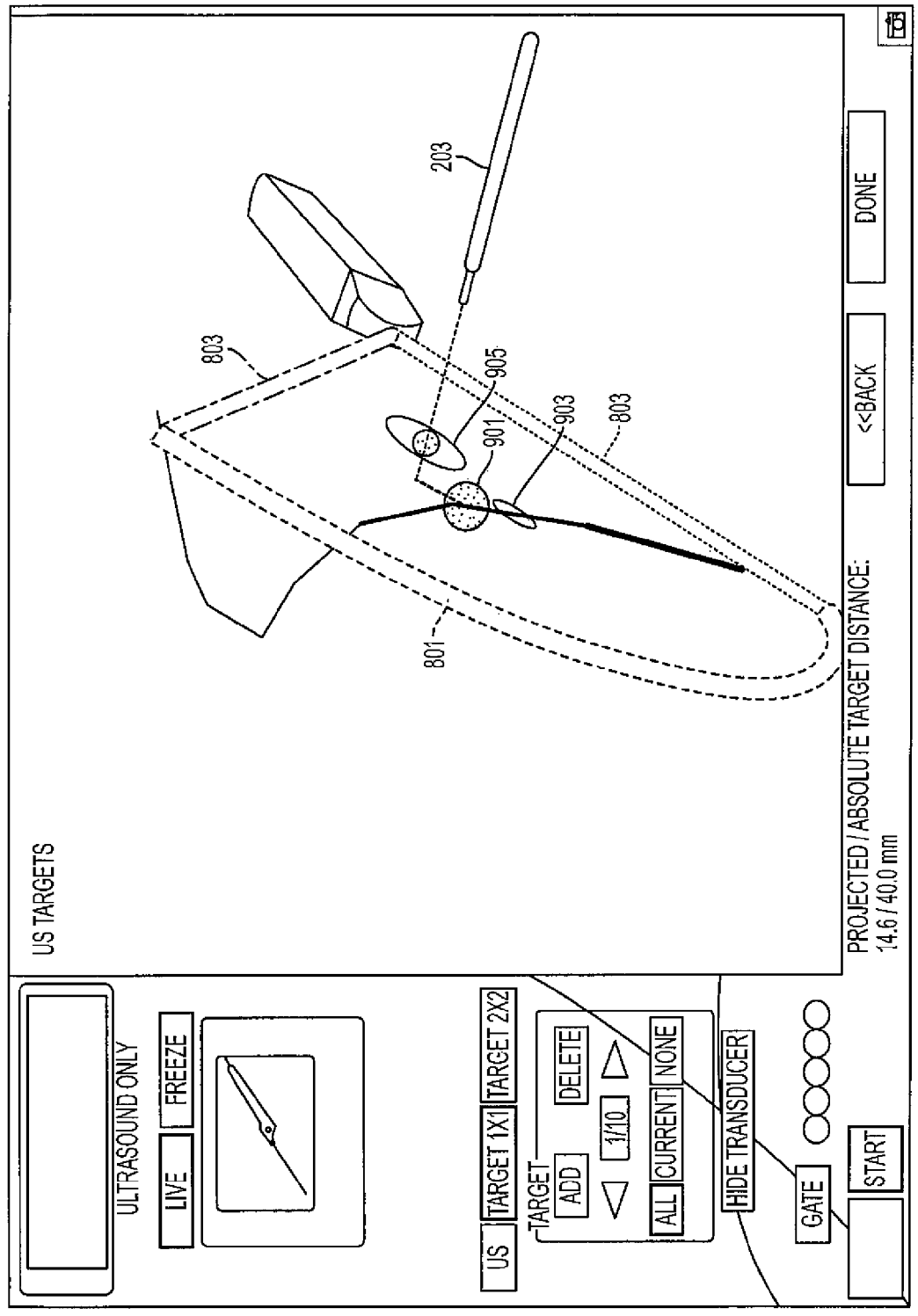
FIG. 9 illustrates an example of a display of a portion of a patient's anatomy including a target vessel relative to a puncture needle, according to various embodiments of the invention.

FIG. 9 illustrates a display 900 which is an example of an enlarged view of the information displayed in FIG. 8. Display 900 illustrates the ultrasound transducer's imaging plane via arch 801 and legs 803 forming a plane and puncture needle 203. Sphere 901 indicates a threshold distance from portal vein (e.g., 2.5 mm). Circle 903 indicates where the ultrasound transducer scan plane will image the portal vein. Circle 905 illustrates where the current trajectory of puncture needle will intersect with the scan plane.

While the systems, processes, and features disclosed herein discuss the invention as used in conjunction with a TIPS procedure to bridge the hepatic and portal veins of a patient (wherein the portal vein is considered a "target vessel"), the systems, processes, and features disclosed herein may be used for other procedures in the anatomy of a patients wherein other elements of the patient's anatomy may be considered "targets."

In some embodiments, the invention may include a computer readable medium that includes instructions causing one or more processors (e.g., processor 103) to perform some or all of the operations, features, and/or functions of the invention.

System 100 is an exemplary system configuration. Other configurations may exist. For example, one or more computer elements, processors, memory devices, display devices, input devices, tracking devices, imaging devices, needles, catheters, cannulas, and/or other elements may be used. Those having skill in the art will appreciate that the invention described herein may work with various system configurations. Accordingly, more or less of the aforementioned system components may be used and/or combined in various embodiments. In some embodiments, as would be appreciated, the functionalities described herein may be implemented in various combinations of hardware and/or firmware, in addition to, or instead of, software. In some embodiments, the operations of the processes described herein may be performed in an order different from the order described herein. In some embodiments, one or more operations may be omitted or combined. In some embodiments, one or more additional operations may be added.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A method for assisting an image-guided transvascular shunting procedure between a first vessel and a target vessel in a portion of an anatomy of a patient using a needle assembly, the needle assembly including a puncture needle slidably mounted within a guide needle, wherein the puncture needle includes at least one position indicating element thereon, a tracking device that samples position and orientation information regarding the at least one position indicating element, and a display device, the method comprising the acts of:

receiving one or more images of the portion of the anatomy of the patient;

determining, using at least the one or more images, a path of the target vessel in three dimensions;

receiving, from the tracking device, position and orientation information regarding the at least one position indicating element after the needle assembly has been navigated into to the first vessel;

determining a position of the puncture needle relative to the target vessel using the sampled position and orientation information regarding the at least one position indicating element; and displaying, on the display device:

the position of the puncture needle relative to the target vessel, a projected path of the puncture needle, the projected path including a path of the puncture needle will follow if the puncture needle is extended past a distal end portion of the guide needle, a point at which the puncture needle will intersect the target vessel if the projected path of the puncture needle intersects the determined path of the target vessel, an indicator of a closest approach from the puncture needle to the target vessel if the projected path of the puncture needle does not intersect the determined path of the target vessel, a numerical value for a projected target distance that represents a distance from a point on the projected path of the puncture needle to a point on the target vessel, wherein the numerical value is zero when the projected path of the puncture needle intersects the target vessel, and a further numerical value for an absolute target distance that represents an actual distance from the puncture needle to the target vessel such that the further numerical value is zero when the puncture needle intersects the target vessel, wherein the numerical value and the further numerical value are simultaneously displayed.

2. The method of claim 1, wherein determining a path of the target vessel further comprises:

receiving patient space data regarding the portion of the anatomy of the patient, and registering the one or more images to the patient space data, wherein the one or more images include data regarding one or more fiducial markings and wherein the patient space data includes data regarding the one or more fiducial markings.

3. The method of claim 1, wherein the one or more images of the portion of the anatomy of the patient are obtained using an ultrasound device, wherein one or more position indicating elements are associated with the ultrasound device, and wherein the one or more position indicating elements associated with the ultrasound device are tracked by the tracking device.

4. The method of claim 3, wherein the act of determining the path of the target vessel in three dimensions further comprises identifying the target vessel, if present, in each of the plurality of images and using calibration information of a scan plane of the ultrasound device and the one or more position indicating elements associated with the ultrasound device to determine the path of the target vessel in three dimensions in a frame of reference of the tracking device.

5. The method of claim 1, wherein the act of determining the path of the target vessel in three dimensions further comprises segmenting the path of the target vessel.

6. The method of claim 1, wherein the act of determining the path of the target vessel in three dimensions further comprises determining a plurality of points forming a centerline of the target vessel.

7. The method of claim 1, wherein the path of the target vessel in three dimensions comprises a series of points smoothed or linked by a piecewise linear or bicubic spline.

8. The method of claim 1, wherein the at least one position indicating element is located at a distal tip portion of the puncture needle.

9. The method of claim 1, further comprising displaying a sphere indicating a predetermined distance from the target vessel.

10. A system for performing an image-guided transvascular shunting procedure between a first vessel and a target vessel in a portion of an anatomy of a patient, the system comprising:

a needle assembly comprising:

a first elongated needle portion comprising a hollow tube having a bend toward a distal tip of the first elongated needle portion, a second elongated needle portion that includes at least one position indicating element at a distal tip of the second elongated needle portion, the second elongated needle portion being slidably mounted within the hollow tube of the first elongated needle portion such that the distal tip of the second elongated needle portion is able to be extended from an opening in the distal tip of the first elongated needle portion in a direction that is substantially tangent to a terminal portion of the bend of the first elongated needle portion, and a fluid flow lumen portion that permits fluid flow between a distal tip of the fluid flow lumen portion and an external portion of the needle assembly; and one or more processing devices configured to:

determine, using one or more images of the portion of the anatomy of a patient, a path of the target vessel in three dimensions;

produce, based at least in part on position and orientation information regarding the at least one position indicating element and the determined path of the target vessel, a display of:

a position of the puncture needle relative to the target vessel, a projected path of the puncture needle, the projected path including a path of the puncture needle will follow if the puncture needle is extended past the distal tip of the first elongated needle portion, a point at which the puncture needle will intersect the target vessel if the projected path of the puncture needle intersects the determined path of the target vessel, an indicator of a closest approach from the puncture needle to the target vessel if the projected path of the puncture needle does not intersect the determined path of the target vessel, a numerical value for a projected target distance that represents a distance from a point on the projected path of the puncture needle to a point on the target vessel, wherein the numerical value is zero when the projected path of the puncture needle intersects the target vessel, and a further numerical value for an absolute target distance that represents an actual distance from the puncture needle to the target vessel such that the further numerical value is zero when the puncture needle intersects the target vessel, wherein the numerical value and the further numerical value are simultaneously displayed.

11. The system of claim 10, wherein the fluid flow lumen is formed by a hollow portion of the second elongated needle portion and wherein the at least one position indicating element comprises a wire coil wrapped around the second elongated needle portion.

12. The system of claim 10, wherein the fluid flow lumen comprises a catheter portion surrounding the second elongated needle portion, wherein the second elongated needle portion is removed from the catheter portion to enable fluid to flow through the fluid flow lumen, and wherein the at least one position indicating element is embedded within the second elongated needle portion.

13. The system of claim 10, wherein the one or more processing devices are further configured to segment the path of the target vessel.

14. The system of claim 10, wherein the one or more processing devices are further configured to determine a plurality of points forming a centerline of the target vessel.

15. The system of claim 10, wherein the path of the target vessel in three dimensions comprises a series of points smoothed or linked by a piecewise linear or bicubic spline.

16. The system of claim 10, wherein the first elongated needle portion is shapeable by a user so as to direct the second elongated needle portion when extended from the opening in the distal tip of the first elongated needle portion.

17. The system of claim 10, wherein the second elongated needle portion comprises a flexible shape-memory material having a straight shape so that the puncture needle returns to the straight shape after exiting from the terminal portion of the bend of the first elongated needle portion to extend in the direction that is substantially tangent to the terminal portion of the bend.

18. A system for assisting an image-guided transvascular shunting procedure between a first vessel and a target vessel in a portion of an anatomy of a patient, the system comprising:

a needle assembly comprising:
a first elongated needle portion comprising a hollow tube having a bend toward a distal tip of the first elongated needle portion,
a second elongated needle portion that includes at least one position indicating element at a distal tip of the second elongated needle portion, the second elongated needle portion being slidably mounted within the hollow tube of the first elongated needle portion such that the distal tip of the second elongated needle portion is able to be extended from an opening in the distal tip of the first elongated needle portion in a direction that is substantially tangent to a terminal portion of the bend of the first elongated needle portion, and
a fluid flow lumen portion that permits fluid flow between a distal tip of the fluid flow lumen portion and an external portion of the needle assembly;

a tracking device that samples position and orientation information of the at least one position indicating element; and one or more processing devices configured to:
determine, using one or more images of the portion of the anatomy of a patient, a path of the target vessel in three dimensions;
receive, from the tracking device, position and orientation information regarding the at least one position indicating element after the needle assembly has been navigated into to the first vessel;
determine a position of the puncture needle relative to the target vessel using the position and orientation information regarding the at least one position indicating element; and
produce, based at least in part on the position and orientation information regarding the at least one position indicating element and the determined path of the target vessel, a display of:
the position of the puncture needle relative to the target vessel,
a projected path of the puncture needle, the projected path including a path of the puncture needle will follow if the puncture needle is extended past the distal tip of the first elongated needle portion,
a point at which the puncture needle will intersect the target vessel if the projected path of the puncture needle intersects the determined path of the target vessel,
an indicator of a closest approach from the puncture needle to the target vessel if the projected path of the puncture needle does not intersect the determined path of the target vessel,
a numerical value for a projected target distance that represents a distance from a point on the projected path of the puncture needle to a point on the target vessel, wherein the numerical value is zero when the projected path of the puncture needle intersects the target vessel, and
a further numerical value for an absolute target distance that represents an actual distance from the puncture needle to the target vessel such that the further numerical value is zero when the puncture needle intersects the target vessel wherein the numerical value and the further numerical value are simultaneously displayed.

* * * * *